United States Patent
Boese et al.

(10) Patent No.: US 8,103,075 B2
(45) Date of Patent: Jan. 24, 2012

(54) METHOD FOR PROVIDING EXTENDED POSSIBILITIES WHEN IMAGING A PATIENT'S HEART

(75) Inventors: Jan Boese, Eckental (DE); Joachim Hornegger, Effeltrich (DE); Günter Lauritsch, Erlangen (DE); Marcus Prümmer, Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 1008 days.

(21) Appl. No.: 12/070,884

(22) Filed: Feb. 21, 2008

(65) Prior Publication Data
US 2008/0205726 A1 Aug. 28, 2008

(30) Foreign Application Priority Data
Feb. 23, 2007 (DE) .......................... 10 2007 009 019

(51) Int. Cl.
*G06K 9/00* (2006.01)

(52) U.S. Cl. .......................................... 382/130; 378/8

(58) Field of Classification Search .................. 382/128, 382/130–132; 378/8, 62
See application file for complete search history.

(56) References Cited

U.S. PATENT DOCUMENTS

| | | | |
|---|---|---|---|
| 5,287,276 | A | 2/1994 | Crawford et al. |
| 2004/0136490 | A1 | 7/2004 | Edic et al. |
| 2006/0133564 | A1 | 6/2006 | Langan et al. |
| 2007/0030945 | A1 | 2/2007 | Boese et al. |

FOREIGN PATENT DOCUMENTS

| | | |
|---|---|---|
| DE | 10 2004 048 209 B3 | 9/2005 |
| DE | 102005016472 A1 | 10/2006 |

OTHER PUBLICATIONS

Jan Modersitzki, "Curvature Registration", Numerical Methods for Image Registration: Chapter 12, 2004, pp. vii-viii, ix-x, 163-174, Oxford University Press, New York, 2004, ISBN: 0198528418.

(Continued)

*Primary Examiner* — Courtney Thomas

(57) ABSTRACT

The invention relates to the use of 2D projection images which belong to a specific common heart phase. A 3D image data set can be used to generate a reference projection image for the same projection angle for each of the 2D projection images and a differential image can be derived from the reference projection image and 2D projection image. The differential images are back-projected and combined in one 3D differential image data set and, by using this, a deformed 3D image data set is obtained from the previously recorded 3D image data set. Iterations guarantee that the deformed 3D image data set ensues with the smallest possible distance from the 2D projection images for the existing common heart phase. Finally, a 3D image data set is available for a different heart phase other than the reference heart phase and the possibilities for imaging a patient's heart are extended.

14 Claims, 1 Drawing Sheet

OTHER PUBLICATIONS

Marcus Prümmer, Jingfeng Han, Joachim Hornegger, "2D-3D Non-rigid Registration using Iterative Reconstruction", 10$^{th}$ International Fall Workshop, Vision Modeling and Visualization 2005, Erlangen, Germany, Nov. 16-18, 2005, pp. 187-194, 3-89838-068-8.

M. Prümmer, J. Hornegger, M. Pfister, A. Dörflerb, "Multi-modal 2D-3D Non-rigid Registration", Medical Imaging 2006: Image Processing, edited by Joseph M. Reinhardt, Josien P. W. Pluim, Proceedings of SPIE, 2006, pp. 1-12, vol. 6144.

Günter Lauritsch, Jan Boese, Lars Wigström, Herbert Kemeth and Rebecca Fahrig; Towards Cardiac C-Arm Computed Tomography Günter Lauritsch et al.; IEEE Transactions on Medical Imaging, vol. 25, No. 7, Jul. 2006, pp. 922-934; Others; 2006.

Marcus Prümmer, Lars Wigström, Joachim Hornegger, Jan Boese, Guenter Lauritsch, Norbert Strobel, Rebecca Fahrig; Cardiac C-arm CT: Efficient Motion Correction for 4D-FBP Prümmer et al.; submission to the SPIE Medical Imaging Conference, San Diego, CA, USA, Oct. 29-Nov. 4, 2006; Others; 2006.

Lilla Zöllei, E. Grimson, A. Norbash, W. Wells; 2D-3D Rigid Registration of X-Ray Fluoroscopy and CT Images Using Mutual Information and Sparsely Sampled Histogram Estimators Lilla Zöllei et al.; IEEE CVPR, 2001, p. 696; Others; 2001.

Andre P. Gueziec; Assessing the registration of CT-scan data to intraoperative x rays by fusing x rays and preoperative information Gueziec; Proc. SPIE vol. 3661, pp. 868-879, Medical Imaging 1999: Image Processing, Kenneth M. Hanson; Ed.; Book; 1999.

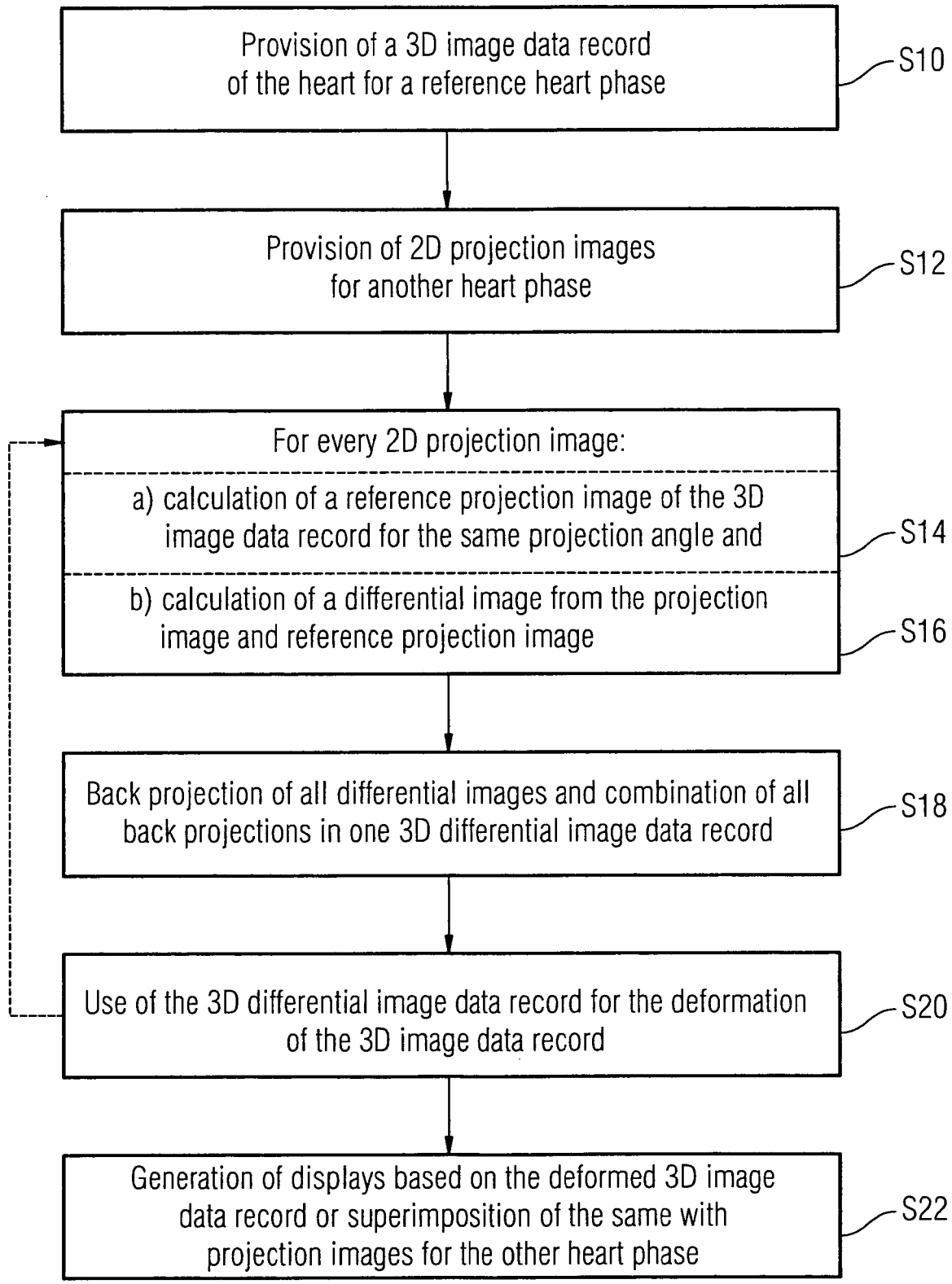

METHOD FOR PROVIDING EXTENDED POSSIBILITIES WHEN IMAGING A PATIENT'S HEART

CROSS REFERENCE TO RELATED APPLICATIONS

This application claims priority of German application No. 10 2007 009 019.8 filed Feb. 23, 2007, which is incorporated by reference herein in its entirety.

FIELD OF THE INVENTION

The invention relates to a method for providing extended possibilities when imaging a patient's heart, in particular during a medical intervention.

BACKGROUND OF THE INVENTION

Medical interventions on the heart of a patient are frequently performed with the aid of a catheter. To assist the doctor in the introduction of a catheter, the intervention is regularly performed in the environment of an X-ray recording system, e.g. the patient lies on a bed in an C-arm X-ray system. This enables 2D X-ray projection images to be recorded during the intervention. During this, the doctor selects the so-called projection angle, i.e. the settings of the C-arm X-ray, suitably to enable him to see a catheter as optimally as possible.

To assist the doctor, also known is the provision of images of the heart which were taken before the intervention. It is precisely with imaging of the heart that is has been found to be a problem that the heart is subject to continuous movement. In this regard, it has been found to be advantageous if, during the recording of the images generated for the generation of the 3D X-ray image data set, an electrocardiogram is recorded so that a phase in the electrocardiogram can be assigned to each image. To be more precise, a cyclically repeated curve in the electrocardiogram is divided into a plurality of intervals each defining a phase. The image data is then sorted according to the phases with a 3D image data set being generated for each phase. More details on this may be found in the patent DE 10 2004 048 209 B3.

Also known are methods for motion correction when imaging the beating heart. In such methods, the images recorded for the generation of the 3D X-ray image data set are assigned calculated motion information relating to a previously selected reference heart beat phase. During the reconstruction of the 3D X-ray image data set from these two-dimensional images, the motion relative to the selected reference state is mathematically corrected in a suitable way so that a high-quality image of the heart for the selected reference phase is obtained. More details on this may be found in patent applications US 2004/0136490 A1 and US 2006/0133564 A1. The U.S. Pat. No. 5,287,276 discloses a comparable method which is used to correct the respiratory movement of the thorax determined by means of a sensor during the recording of the images required for the generation of a 3D X-ray image data set.

During the image recording, the heartbeat phase can be used to trigger the recording of the images so that the 3D X-ray image data set for a selected reference phase is of particularly high quality, while other phases tend to be ignored.

Therefore the outcome of the methods claimed in the prior art is that a 3D X-ray image data set of the heart is provided which is assigned to a reference phase in the electrocardiogram of the heart. However, during the intervention, it may be the case that the 2D projection images recorded are not assigned to this reference phase. It is possible that this doctor performing the treatment does not even want this. In this case, it would not be advantageous to generate pictures from the 3D X-ray image data set assigned to the reference phase, which are, for example, superimposed on the 2D X-ray projection images which are assigned to another phase in the electrocardiogram of the heart.

SUMMARY OF THE INVENTION

The object of the invention is to extend the possibilities when imaging a patient's heart so that the doctor performing the treatment is given optimum support from imaging during the treatment.

The object is achieved by a method with the features claimed in the claims.

Hence, the inventive method starts with above-described situation in which a 3D X-ray image data set of the heart is provided which is assigned to a reference phase in the electrocardiogram of the heart and that a plurality of 2D X-ray projection images is provided all of which are assigned to the same phase in the electrocardiogram of the heart, with, generally, this same phase not being identical to the reference phase. Then, a 2D reference projection image is generated for each of the 2D X-ray projection images from the 3D X-ray image data set. Since the projection angle defined by the X-ray image recording system is known, it is possible to calculate a 2D projection image of this kind for precisely this projection angle by calculating a forward projection from the 3D X-ray image data set. In the next substep, a 2D differential image is then calculated between the 2D X-ray projection image and the reference projection image. A differential image is nothing other than an image in which, for a predefined pixel, the gray-scale value of the one image is determined and then the gray-scale value of the other image and wherein these gray-scale values are subtracted from each other and this calculated difference is then the image entry, that is the gray-scale value, for the predefined pixel of the 2D differential image.

Hence, a plurality of 2D differential images is obtained, namely for each of the plurality of 2D X-ray projection images which are usually recorded during the medical intervention. Subsequently, all the 2D differential images are back-projected. The back projection is a measure known from the prior art in which 2D projection images are imaged on volume elements (voxels), with once again gray-scale values being assigned to the volume elements. The back projections are then all combined in one 3D differential image data set. Usually, it is then only necessary to add up the gray-scale values from the voxels of the individual back projections and the total is then normalized. This 3D differential image data set is then used for the deformation of the 3D X-ray image data set. For this, it is possible to use methods known per-se for deformation. In one example of a method of this kind, a gradient field is calculated from the 3D X-ray image data set and multiplied voxelwise with the 3D differential image data set. This obtains so-called "force vectors" which indicate how grid points, for which the 3D X-ray image data set is defined, have to be displaced. A deformed image data set is an image data set in which the underlying pixel grid is deformed. Preferably, the deformed image data set should result from a minimization of distances with respect to the 2D projection images. For this, the steps of the generation of the 2D reference projection images, namely from the deformed 3D X-ray image data set, the calculation of the 2D differential images and the back projection of the 2D differential images will be repeated until a predefined measure for the 3D differential image data set reaches (and/or falls below/exceeds) a predefined limit value. The predefined measure should indicate the size of the distance between the deformed image data and the 2D projection image data.

The provision of finished deformed 3D image data set overcomes the problem of the prior art in that during the intervention only one 3D X-ray image data set is provided which is assigned to a specific reference phase in the electrocardiogram. Instead, the deformed 3D image data set is assigned to the phase in the electrocardiogram of the heart to which the 2D X-ray projection images are assigned. This creates extended possibilities, which was the object of the inventive method. These possibilities are then preferably used in that the deformed 3D image data set is used for imaging the patient's heart.

Usually, this imaging consists of a 2D projection image being calculated for any projection angle for which no recording was generated. This benefits the doctor performing the treatment in that he does not have to continuously record new 2D projection images but can have any projection images he desires calculated on the basis of the deformed 3D image data set. It is conceivable that doctor performing the treatment could define the projection angle by moving a computer mouse and receive changing projection images on a screen depending on the position of the mouse. It is particularly advantageous if the calculated 2D projection image is superimposed on another 2D image, e.g. an image recorded during the intervention. The latter image can then for example show a catheter which is used during the intervention, while the superimposed image shows the heart without the catheter. The superimposed image is able to depict the structures of the heart much more clearly, while for the 2D image onto which the image is superimposed it is sufficient for the catheter to be clearly visible.

A second type of use for the extended possibilities during imaging consists of simultaneously generating a 4D-image data set. For this, the 2D X-ray projection images must be provided for a plurality of phases in the electrocardiogram of the heart and for each of these phases a deformed 3D image data set must be provided using 2D differential images and a 3D differential image data set derived therefrom. Hence, a plurality of deformed 3D image data sets are obtained, namely one for each of the plurality of phases in the electrocardiogram of the heart. These phases can then be placed in a sequence and an image can then be generated from each of the deformed 3D image data sets in this sequence. Then, a sequence of images is obtained corresponding to the sequence of the phases in the electrocardiogram. This sequence can, for example, be played back like a film so that the doctor performing the treatment can see the heart actually beating.

BRIEF DESCRIPTION OF THE DRAWINGS

A preferred embodiment of the invention is described below with reference to the drawing, with the FIGURE depicting the steps of the inventive method.

DETAILED DESCRIPTION OF THE INVENTION

The inventive method starts with step S10 in which a 3D image data set of the heart is provided for a reference heart phase. The FIGURE does not expressly mention that the images are X-ray images, but the method is especially useful if exclusively X-ray images are used. In the next step, S12, 2D projection images are provided for another heart phase. Each 2D projection image is assigned a projection angle defining the projection as such which results from the settings of the X-ray image recording system used. The projection angle can frequently be defined as a tilting angle of a C-arm X-ray. Now, in step S14, a reference projection image of the 3D image data set is calculated for each 2D projection image in step S14 for precisely the projection angle which is assigned to the 2D projection image. This is also known as "forward projecting" of the 3D image data set. In step S16, a differential image is then calculated from the projection image and the reference projection image.

The differential images are all back-projected in step S18, with all back projections being combined in one 3D differential image data set. Here, the gray-scale values of the differential images are averaged volume-element-wise, i.e. added up and normalized volume-element-wise. In the following step, S20, the 3D differential image data set is used for the deformation of the 3D image data set. A method which is known per se is used for the deformation. Examples of methods for deformation may be found in the book by J Modersitzki, "Numerical Methods for Image Registration", Oxford University Press, 2004, ISDN 10:0198528418. In the present case, for example, a known deformation method can be used in which a 3D gradient vector is calculated for the 3D image data set to be deformed for each voxel. These vectors are then multiplied voxelwise with the respective gray-scale values from the 3D differential image data set. The vector field obtained in this way then represents the "force vector field" with the aid of which the individual grid points, for which the voxels are defined, are displaced. The vector defines the direction of the displacement of the grid point and the degree of the displacement. Depending upon whether a measure for the 3D differential image data set indicates that the gray-scale values are sufficiently small or not, steps S14 to S20 are repeated or the method moves on to step S22. The reason for the iteration of steps S14 to S20 is to minimize a distance so that overall the effect of an elastic registration is obtained. After the final completion of step 20, a deformed 3D image data set finally provides extended possibilities for imaging of the patient, since this deformed 3D image data set is assigned to the other heart phase, to which the 2D projection images are assigned, and not to the reference heart phase. These extended possibilities include the fact that displays based on the deformed 3D image data set can be generated, e.g. simple 2D projection images for any projection angles. In particular, such displays can also be superimposed with projection images for the other heart phase (or for other heart phases), with it being possible to use conventional methods for the superimposition of images.

Not shown in the FIGURE is the fact that steps S12 to S20 can be repeated for a plurality of heart phases which differ from the reference heart phase. Each time step S20 is reached (in the last iteration of the repetition of steps S14 to S20 in each case), a deformed 3D differential image data set is obtained. On the basis of the plurality of 3D differential image data sets, it is then possible to determine a temporal sequence by sorting according to the heart phase and displays based on the 3D differential image data sets can be played back in a short temporal sequence like a film.

Advantageously, in a special application for imaging a heart, the present invention uses methods of elastic alignment, such as those described in the article by M. Prümmer, J. Han and J. Hornegger: "2D-3D Non-rigid Registration using Iterative Reconstruction", G. Greiner, J. Hornegger, H. Niemann, M. Stamminger, editors, Vision, Modeling, and Visualization 2005, Berlin, November 2005, Akademische Verlagsgesellschaft Aka GmbH or also in the article by M. Prümmer, J. Hornegger, T. Kuwert, "Multimodal 2D-3D Non-rigid Registration", Proc. SPIE Vol. 6144, February 2006, San Diego.

The invention claimed is:

1. A method for imaging a heart of a patient, comprising:
providing a 3D X-ray image data set of the heart assigned to a reference phase in an electrocardiogram of the heart;
providing a plurality of 2D X-ray projection images of the heart assigned to a same phase with each other in the electrocardiogram of the heart;
calculating a plurality of 2D reference projection images from the 3D X-ray image data set each corresponding to one of the 2D X-ray projection images for a same projection angle;
calculating a plurality of 2D differential images each between one of the 2D X-ray projection images and the corresponding one of the 2D reference projection images;
back projecting the 2D differential images;
combining the back projections into a 3D differential image data set;
deforming the 3D X-ray image data set using the 3D differential image data set; and
imaging the heart of the patient using the deformed 3D X-ray image data set.

2. The method as claimed in claim 1, wherein the deformed 3D-X-ray image data set is iteratedly calculated based on 2D reference projection images calculated from a deformed 3D-X-ray image data set in a preceding iteration loop until a predefined measure for the 3D differential image data set reaches a predefined limit value.

3. The method as claimed in claim 1, wherein a 2D projection image for any projection angle is calculated by the deformed 3D image data set.

4. The method as claimed in claim 3, wherein the calculated 2D projection image is superimposed on anther 2D X-ray image recorded during imaging the heart.

5. The method as claimed in claim 1, wherein a sequence of 2D X-ray projection images of the heart are provided for a sequence of different phases in the electrocardiogram of the heart.

6. The method as claimed in claim 5, wherein a plurality of deformed 3D image data sets are calculated in accordance with the sequence of the phases in the electrocardiogram based on the sequence of the 2D X-ray projection images.

7. The method as claimed in claim 1, wherein the reference phase in the electrocardiogram of the 3D X-ray image data set is different than the same phase in the electrocardiogram of the heart of the 2D X-ray projection images.

8. A medical device for imaging a heart of a patient, comprising:
an X-ray imaging device that records a plurality of 2D X-ray projection images of the heart assigned to a same phase with each other in an electrocardiogram of the heart;
a memory that stores a 3D X-ray image data set of the heart assigned to a reference phase in the electrocardiogram of the heart; and
a computer that:
calculates a plurality of 2D reference projection images from the 3D X-ray image data set each corresponding to one of the 2D X-ray projection images for a same projection angle,
calculates a plurality of 2D differential images each between one of the 2D X-ray projection images and the corresponding one of the 2D reference projection images,
back projects the 2D differential images,
combines the back projections into a 3D differential image data set, and
deforms the 3D X-ray image data set using the 3D differential image data set for imaging the heart of the patient.

9. The medical device as claimed in claim 8, wherein the computer iteratedly calculates the deformed 3D-X-ray image data set based on 2D reference projection images calculated from a deformed 3D-X-ray image data set in a preceding iteration loop until a predefined measure for the 3D differential image data set reaches a predefined limit value.

10. The medical device as claimed in claim 8, wherein a 2D projection image for any projection angle is calculated by the deformed 3D image data set.

11. The medical device as claimed in claim 10, wherein the calculated 2D projection image is superimposed on anther 2D X-ray image recorded during imaging the heart.

12. The medical device as claimed in claim 8, wherein a sequence of 2D X-ray projection images of the heart are recorded for a sequence of different phases in the electrocardiogram of the heart.

13. The medical device as claimed in claim 12, wherein a plurality of deformed 3D image data sets are calculated in accordance with the sequence of the phases in the electrocardiogram based on the sequence of the 2D X-ray projection images.

14. The medical device as claimed in claim 8, wherein the reference phase in the electrocardiogram of the 3D X-ray image data set is different than the same phase in the electrocardiogram of the heart of the 2D X-ray projection images.

* * * * *